United States Patent [19]

Arcamone et al.

[11] 4,077,988

[45] Mar. 7, 1978

[54] OPTICALLY ACTIVE ANTHRACYCLINONES

[75] Inventors: Federico Arcamone, Nerviano; Luigi Bernardi, Milan; Bianca Patelli, Milan; Aurelia Di Marco, Milan, all of Italy

[73] Assignee: Societa' Farmaceutici Italia, S.p.A., Milan, Italy

[21] Appl. No.: 649,825

[22] Filed: Jan. 16, 1976

[30] Foreign Application Priority Data

Jan. 22, 1975 United Kingdom ............... 02691/75

[51] Int. Cl.$^2$ ....................... C07C 49/68; C07C 49/72; A61K 31/12
[52] U.S. Cl. .................................... 260/376; 260/365; 260/345.9 R; 424/331; 424/283
[58] Field of Search ................. 260/365, 383, DIG. 8, 260/376

[56] References Cited

U.S. PATENT DOCUMENTS 3,904,632  9/1975  Hollander ...................... 260/DIG. 8

OTHER PUBLICATIONS

Wong et al., "......Daunomycinone" Canadian J. Chem. Canada, vol. 49, No. 16 (9/1971), pp. 2712-2718.

Primary Examiner—Daniel E. Wyman
Assistant Examiner—Thomas A. Waltz
Attorney, Agent, or Firm—Hubbell, Cohen, Stiefel & Gross

[57] ABSTRACT

Disclosed are optically active anthracyclinones and their daunosaminyl derivatives, which are useful for the treatment of malignant diseases, particularly sarcomas, breast cancer, bronchogenic carcinoma, malignant lymphomas, neuroblastomas, acute leukemia and bladder cancer.

2 Claims, No Drawings

OPTICALLY ACTIVE ANTHRACYCLINONES

CROSS-REFERENCE TO RELATED APPLICATION

This application is related to and incorporates by reference the entire contents of applications, Ser. No. 560,105 (now U.S. Pat. No. 4,039,663), 568,437 (now abandoned) and 579,901 (now U.S. Pat. No. 4,046,878), filed respectively on Mar. 19, 1975; Apr. 16, 1975; and May 22, 1975, all of which are owned by the assignee hereof.

BACKGROUND OF THE INVENTION

1. Field of the Invention

The invention relates to certain novel optically active anthracyclinones of the daunomycin group, daunosaminyl derivatives of said compounds and methods for the preparation thereof.

2. The Prior Art

While the optically active anthracyclinones of the invention are novel, the corresponding racemates of certain of them have been described in the literature; see C. M. Wong et al, *Canad.J.Chem.*, 49, 2712 (1971) and *Canad.J.Chem.*, 51, 466 (1973).

SUMMARY OF THE INVENTION

The present invention, in one aspect thereof, relates to a novel class of optically active anthracyclinones of the daunomycin group and to the daunosaminyl derivatives thereof. In another aspect, the invention relates to methods for the preparation of such compounds.

These compounds are useful for the treatment of malignant diseases, particularly sarcomas, breast cancer, bronchogenic carcinoma, malignant lymphomas, neuroblastomas, acute leukemia and bladder cancer. The novel anthracyclinones of the invention are otpically active compounds of the general formulae IV', IV''', VIII', VIII'', VIII''' and VIII'''':

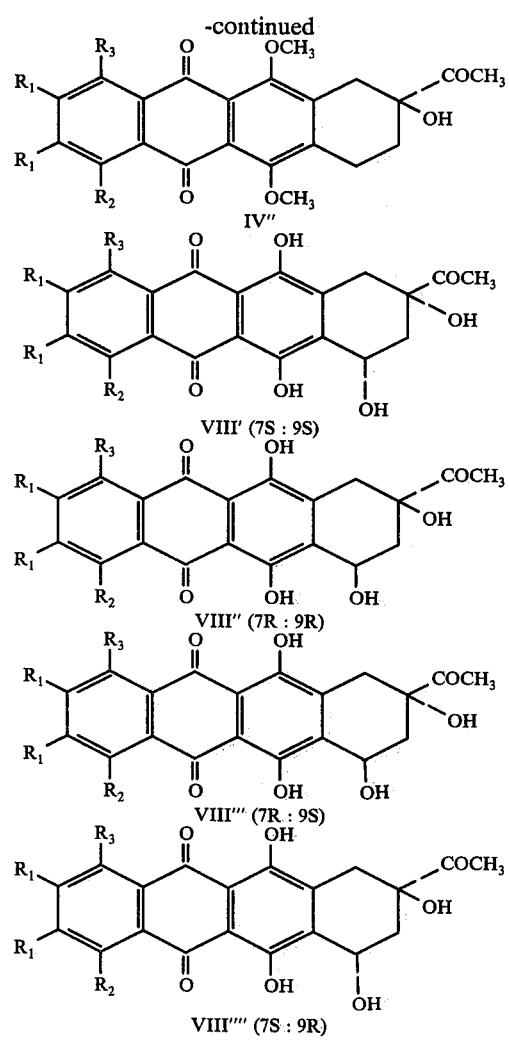

wherein (a) $R_1$ is hydrogen and $R_2$ and $R_3$ are the same and are hydrogen, methyl, methoxy, chlorine or bromine;

(b) $R_2$ and $R_3$ are both hydrogen and $R_1$ is methyl, methoxy, chlorine or bromine; or (c) $R_1$ and $R_3$ are both hydrogen and $R_2$ is methoxy.

The above optically active anthracyclinones of the formulae IV', IV''', VII', VII'', VIII''' and VIII'''' are themselves novel, although some of the corresponding racemates have been described by C. M. Wong et al, supra. The synthesis of the racemates as described by Wong et al proceeds according to the reaction scheme:

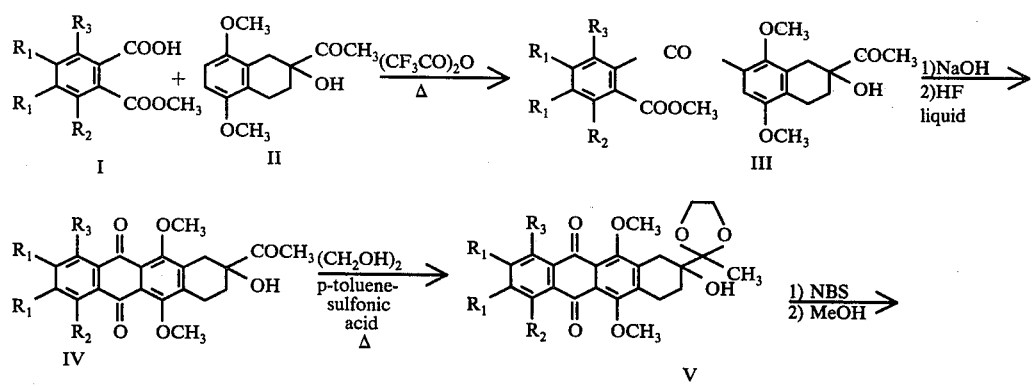

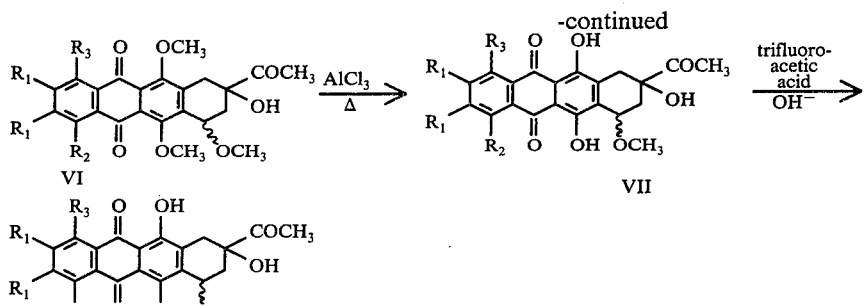

VI

VII

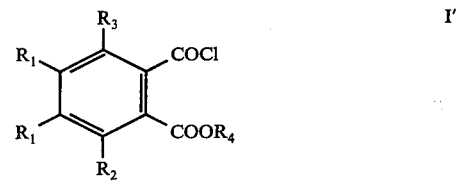

VIII

The above reaction scheme yields anthracyclinones of the general formula VIII in the racemic form, whereas the natural aglycones are optically active and have the 7S : 9S configuration (according to the nomenclature of Cahn, et al, Experientia, 1956, 12, 81).

In order to obtain the natural anthracycline antibiotics and/or their analogues substituted in ring D by condensation of the aglycones with an appropriate derivative of daunosamine according to applications Ser. Nos. 568,437, filed Apr. 16, 1975 (now abandoned) and 579,901, filed May 22, 1975 (now U.S. Pat. No. 4,046,878), it would therefore be preferable to employ optically active aglycones having the 7S : 9S configuration rather than condensing the daunosamine derivative with the racemic aglycone and subsequently separating the (—)daunosaminyl (+)anthracyclinone from the (—)daunosaminyl (—)anthracyclinone, by a troublesome and time consuming procedure such as fractional crystallization or chromatography.

It is known (Eliel, *Stereochemistry of Carbon Compounds*, page 55, — McGraw-Hill, 1962) that the optical resolution of alcohols can be carried out in the best manner through a salt formation of the hemiphthalates with an optically active base. However, the poor solubility of the anthracyclinones VIII and their derivatives in most solvents makes this procedure practically useless. Moreover, from a practical and economical point of view the resolution should be performed at the earliest possible stage in the overall synthesis in order to perform the synthetic procedure on the optically active intermediate already having the required configuration. The first intermediate having the necessary chiral center is the ketol derivative II. Prior to this invention, no method was known for the optical resolution of such a derivative.

This invention accordingly provides a novel process for the optical resolution of a ketol having the general formula II herein, which comprises reacting (—)-1-phenyl-ethylamine with racemic 1,4-dimethoxy-6-hydroxy-6-acetyl-tetralin in a suitable solvent such as acetonitrile to give the diasteroisomeric Schiff bases which are separated by crystallization and from which the enantiomeric ketols II are recovered by acid treatment. The separation is clean-cut and totally unexpected since no previous cases of the resolution of ketones via ketimines have been reported (Eliel, loc. cit., page 56); most probably because Schiff bases are usually rather unstable and decompose easily during crystallization. Moreover, it has now been found that the optically active ketols II can be reconverted into the racemic ketol II and it is therefore possible to convert the racemic ketol II into the required optically active form in very high yield, via the resolution of the racemic keton II with (—)-1-phenyl-ethylamine followed by the reconversion of the unwanted isomer back into the racemic form, and repetition of the optical resolution.

The above reaction scheme proposed by Wong et al, employs, in several of the reaction steps, strongly acidic conditions which favor the racemization of the chiral center via a planar carbocation (Eliel, loc. cit., page 372); and in fact, operating as described by Wong et al on optically active ketol II, the resulting anthraquinone IV is completely devoid of optical activity. The present invention accordingly provides a novel method of synthesizing of the optically active compounds IV' and IV" which comprises condensing an optically active ketol II with an appropriatee phthalic acid monoester monochloride of the general formula I':

I' wherein $R_1$, $R_2$ and $R_3$ are as defined above, and $R_4$ is methyl, ethyl or halosubstituted ethyl, in the presence of a Lewis acid such as anhydrous aluminum chloride in a suitable solvent such as carbon disulphide, dichloromethane, tetrachloroethane, benzene or nitrobenzene to give, after treatment with sodium hydroxide, an optically active benzoyl benzoic acid III. Compound III is then cyclized to the corresponding optically active compound IV' or IV" with liquid hydrogen fluoride or with methanesulphonic acid/$P_2O_5$. The reagent methanesulphonic acid/$P_2O_5$ is disclosed in *J.Org.Chem.*, 38, 4071, (1973).

In view of the easy racemization of the ketol chiral center, the isolation of compounds IV' and IV" in optically active form is quite unexpected.

The optically active compounds IV' and IV" can surprisingly be converted, according to the invention, into the optically active forms of the ketal V without racemization, by treatment with ethylene glycol in the presence of p-toluenesulphonic acid at elevated temperatures. Treatment of the optically active ketal V with N-bromo-succinimide in carbon tetrachloride gives a labile 7-bromo-ketal, which on treatment witth methanol, yields a mixture of 7(S) and 7(R) methyl ethers. These methyl ethers may be demethylated at the 6- and 11-positions by treating same with an aluminum halide, such as aluminum chloride or bromide in a homogeneous solution in chlorobenzene, bromobenzene or nitrobenzene, preferably, nitrobenzene, to produce the demethylated compounds in high yield and in a single step. The amount of aluminum halide used is not critical and can be from 1 to 20 moles per mole of the methyl ether compound, but the best results are obtained with 4-8 moles of aluminum halide. The temperature at which the reaction is conducted can be varied from 0° to 50° C., but the best results are obtained at temperatures of 20° C. or less. This procedure is disclosed in greater detail in U.S. Pat. No. 3,963,760 which coresponds to British Patent No. 1461190. Using this technique, the optical activity of the demethylated compounds is retained; thus there is obtained a mixture of 7(S)- and 7(R)- methoxy anthracyclinones which is then treated with trifluoroacetic acid and subsequently with sodium bicarbonate to give the corresponding 7(S) and 7(R) hydroxy derivatives. These latter are separated by crystallization or by chromatography on silica gel to give the appropriate optically active pure compounds VIII' (7S : 9S configuration), VIII" (7R : 9R configuration) and their 7-epimers, that is VIII'" (7R : 9S configuration) and VIII"" (7S : 9R configuration) in which $R_1$, $R_2$ and $R_3$ are as defined above. The compounds VIII' to VIII"" are novel compounds that are provided by the present invention.

A preparation of the optically active anthracyclinones VIII' according to the invention is described below in greater detail by way of example. The racemic ketol II is condensed with (−)-1-phenylethylamine in a suitable aprotic solvent such as acetonitrile to give a crystalline Schiff base IX.

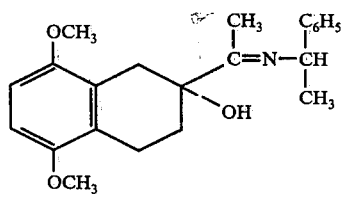

and mother liquors from which, by treatment with dilute acid, the (−) and (+) forms of the ketol II are isolated.

The (−) form of the ketol II is then condensed with an appropriate phthalic acid monoester monochloride in a suitable solvent such as carbon disulphide, dichloromethane, tetrachloroethane, nitrobenzene or benzene in the presence of aluminum trichloride or another Lewis acid to give the corresponding optically active benzoyl benzoate III. This compound III is hydrolyzed with alcholic sodium hydroxide and the resulting acid is then treated with liquid hydrogen fluoride at a temperature of 0° to 25° C. for 3 to 10 hours or with methanesulphonic acid/$P_2O_5$ reagent at 25° C. for 24 hours. The resulting anthraquinone IV' is then treated with diethylene glycol in benzene or ethylene tetrachloride in the presence of a trace of a strong acid such as toluene-sulphonic acid in an apparatus provided with a trap to collect the water formed in the reaction, to give the coresponding optically active ketal V which is then irradiated with a tungsten lamp at reflux in carbon tetrachloride with N-bromo-succinimide for 5 to 15 minutes to give the labile 7-bromoketal. The latter compound is not isolated, and is treated with methanol to yield a mixture of 7(S) and 7(R) methyl ethers VI. This mixture (without purification) is reacted witth aluminum chloride in benzene, nitrobenzene or tetrachloroethane at between 5° and 50° C. for 1 to 10 hours to give a mixture of 7(S) and 7(R) methoxy-anthracyclinones VII. Treatment of VII with trifluoroacetic acid at 5° to 30° C. for 8 to 20 hours and subsequently with sodium bicarbonate for a short time gives anthracyclinones of formula VIII' together with their 7(R) epimers that are separated by crystallization or chromatography to give pure VIII' (cis 7,9 diol diastereomer). The 7(R)-epimer VIII'" (trans 7,9 diol diastereomer) is isolated and eventually recycled together with VII for the trifluoroacetic acid treatment. Similarly, from the (+) form of the ketoln II, operating as above, the compound VIII" (7R : 9R configuration) and its 7(S)-epimer VIII"" (7S : 9R configuration) can finally be obtained.

The invention also provides a process for the synthesis of a compound X, X', XI, XI', XII, XII', XIII and XIII' in which $R_1$, $R_2$ and $R_3$ are as defined above and $R_5$ is H or $COCF_3$. The compounds X, X', XI, XI', XII, XII', XIII and XIII' are also novel compounds provided by the invention.

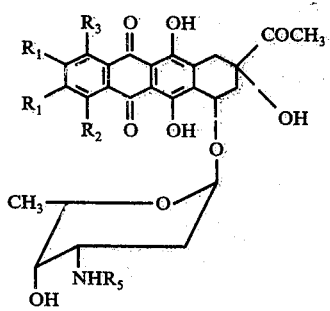

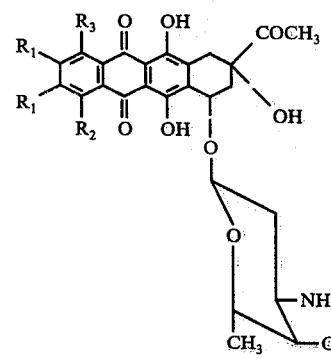

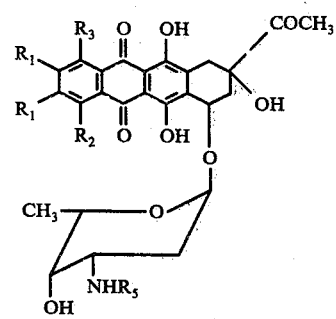

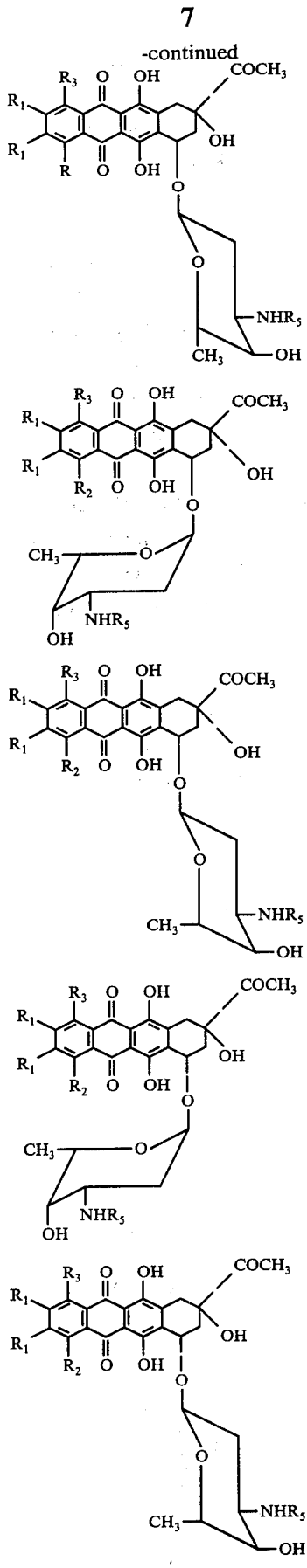

The process for making these latter compounds comprises condensing 2,3,6-trideoxy-3-trifluoroacetamido-4-O-trifluoroacetyl-α-L-lyxopyranosyl chloride as described in application Ser. No. 560,105, filed Mar. 19, 1975 (now U.S. Pat. No. 4,039,663, with an appropriate optically active anthracyclinone VIII' to VIII'''' in an anhydrous solvent in the presence of HgO, HgBr$_2$ and a molecular sieve, or condensing 1,2,3,6-tetradeoxy-4-O-trifluoroacetyl-3-trifluoroacetamido-L-lyxo-hex-1-enepyranose, as described in application Ser. No. 568,437, filed Apr. 16, 1975 (now abandoned), with an appropriate optically active anthracyclinone VIII' to VIII'''' in an anhydrous solvent such as benzene or nitromethane in the presence of p-toluenesulphonic acid, and treating the resulting 7-(4'-O-trifluoroacetyl-3'-trifluoroacetamido-L-lyxo-pyranosyl-) intermediates first with methanol to obtain the coresponding N-trifluoroacetyl derivatives X, X', XI, XI', XII, XII', XIII, XIII' wherein R$_5$ is COCF$_3$ which are isolated as such or are treated successively with 0.1 N NaOH for 30 minutes at room temperature to eliminate the last trifluoroacetyl protecting group on the sugar moiety to thereby finally obtain the desired end products.

In the preparative examples which follow, references to daunomycinones are intended to mean anthracyclinones which have the same configuration (7S : 9S) as natural daunomycinone, and references to 7,9-bis-epi-daunomycinones are intended to mean anthracyclinones with the 7R : 9R configuration. The products of the Examples are novel compounds with the exception of daunomycinone itself.

DESCRIPTION OF THE PREFERRED EMBODIMENTS

The invention will now be described in greater detail in conjunction with the following examples which are not intended to be a limitation of the invention. All parts given are by weight unless otherwise indicated.

EXAMPLE 1

Resolution of 1,4-dimethoxy-6-hydroxy-6-acetyl-tetralin.

13.8 gm. of 1,4-dimethoxy-6-hydroxy-6-acetyl-tetralin in 50 ml. of acetonitrile and 7.4 gm. of (−)-1-phenylethylamine were heated for 5 min. at 80° C. The solution was slowly cooled to room temperature, and after 3 hrs. the crystalline precipitate was collected (6 gm.; m.p. 190°-192°; $[\alpha]_D^{20}$ − 38°, c = 1, CHCl$_3$) and dissolved in 50 ml. of methanol containing 12 ml. of 2 N HCl. The solution was heated at 50° for 10 min., then diluted with water and extracted with chloroform. The chloroform extract was evaporated in vacuo and the residue crystallized from chloroform-ethyl ether to give (−)-1,4-dimethoxy-6-hydroxy-6-acetyl-tetralin (II) (4.3 gm.; m.p. 130°-132°; $[\alpha]_D^{20}$ − 50°, c = 1, CHCl$_3$).

The acetonitrile mother liquors were evaporated in vacuo and the residue taken up in 50 ml. of methanol containing 14 ml. of 2 N HCl. The solution was heated at 50° for 10 min., then diluted with water and extracted with chloroform. The chloroform extract was evaporated in vacuo and the residue crystallized from chloroform-ethyl ether to give (+)-1,4-dimethoxy-6-hydroxy-6-acetyl-tetralin (4.8 gm; m.p. 130°-132°; $[\alpha]_D^{20}$ + 50°, c = 1, CHCl$_3$). From the mother liquors 4.5 gm. of racemic 1,4-dimethoxy-6-hydroxy-6-acetyl-tetralin were recovered by concentration and recycled.

EXAMPLE 2

4-Demethoxy-7-desoxy-daunomycinone dimethyl ether (IV'; $R_1=R_2=R_3=H$).

To 5 gm. of (−)-1,4-dimethoxy-6-hydroxy-6-acetyl-tetralin in 50 ml. of dichloromethane, 20 gm. of phthalic acid methyl ester monochloride were added and, over a period of 1 hour, 15 gm. of AlCl₃ were slowly added thereto with constant stirring at room temperature. The suspension was kept at room temperature for 2 hrs. and then poured onto ice.

The solution was extracted with chloroform and the extracts washed with water and with dilute NaHCO₃ solution. The chloroform extracts were evaporated in vacuo and the oily residue was taken up in 100 ml. of 60% ethanol containing 8 gm. of NaOH. The solution was kept at 60° for one hour, then diluted with water and extracted with chloroform. By evaporation of the chloroform extracts, (−)-1,4-dimethoxy-6-hydroxy-6-acetyl-tetralin (0.6 gm.; m.p. 130°–132°; $[\alpha]_D^{20} - 50°$, c = 1, CHCl₃) was recovered and recycled. The aqueous solution was acidified with 2 N HCl and extracted with chloroform. Evaporation of the solvent leaves an oily residue (III; $R_1=R_2=R_3=H$; 9 gm.) that was dissolved in 20 ml. of liquid HF. After 3 hrs. the HF was evaporated and the residue taken up in chloroform. The chloroform extract was washed with water and 2 N NaOH and then evaporated in vacuo. The residue was crystallized from ether to give 4.9 gm. of 4-demethoxy-7-desoxy-daunomycinone dimethyl ether (IV'; $R_1=R_2=R_3=H$; m.p. 142°–144°; $[\alpha]_D^{20} - 33°$; c = 1, CHCl₃).

EXAMPLE 3

4-Demethoxy-7-desoxy-9-epi-daunomycinone dimethyl ether (IV''; $R_1=R_2=R_3=H$).

Operating as in Example 2, but employing (+)-1,4-dimethoxy-6-hydroxy-6-acetyl-tetralin, there was obtained 4-demethoxy-7-desoxy-9-epi-daunomycinone dimethyl ether (m.p. 142°–144°; $[\alpha]_D^{20} + 34°$; c = 1, CHCl₃).

EXAMPLE 4

4-Demethoxy-7-desoxy-7-methoxy-daunomycinone (VII; configuration 9S; $R_1=R_2=R_3=H$).

5 gm. of 4-demethoxy-7-desoxy-daunomycinone dimethyl ether dissolved in 500 ml. of benzene containing 10 ml. of ethylene glycol and 0.3 gm. of p-toluenesulfonic acid were refluxed in a Dean-Stark apparatus for 5 hrs. The solution was cooled, 0.5 ml. of pyridine was added, and the solution washed with water. Evaporation of the solvent leaves a residue that is crystallized from ether to give 5 gm. of the ketal V (configuration 9S; $R_1=R_2=R_3=H$; m.p. 175°–177°; $[\alpha]_D^{20} - 29°$, c = 1, CHCl₃). This product was dissolved in 300 ml. of CCl₄ containing 2.5 gm. of N-bromosuccinimide. The solution was heated at reflux for 10 minutes using a 500 watt tungsten lamp. After cooling, the solution was evaporated in vacuo and the residue taken up in 200 ml. of methanol and refluxed for 5 hrs. After evaporation of the solvent, the residue was taken up in 150 ml. of dioxane containing 60 ml. of water and 20 ml. of concentrated HCl. The solution was kept overnight at room temperature, then concentrated in vacuo. The residue was taken up in chloroform, which was washed with water and 5% NaHCO₃, and re-evaporated in vacuo to give 4.8 gm. of raw VI (configuration 9S) as a mixture of the 7(S) and 7(R) epimers. This residue was dissolved in 400 ml. of benzene. 8 gm. of AlCl₃ were added and the suspension stirred for 2 hrs. at 40°. The solution was cooled, 1050 ml. of 3% oxalic acid were added and chloroform was added to complete solution. The organic layer was washed with water and 5% NaHCO₃ and evaporated to dryness. The residue was chromatographed on silica gel. Upon elution with chloroform, 2.8 gm. of 4-demethoxy-7-desoxy-7-methoxy-daunomycinone; (VII, configuration 9S; $R_1=R_2=R_3=H$), as a mixture of the 7(S) and 7(R) epimers, were collected and used, as such in the following example. The pure 7(S) isomer can be obtained by careful chromatography, m.p. 155°–157°; $[\alpha]_D^{20} + 145°$, c = 0.1, dioxane.

EXAMPLE 5

4-Demethoxy-daunomycinone (VIII'; $R_1=R_2=R_3=H$).

1.5 gm. of a mixture of the 7(S) and 7(R) epimers of 4-demethoxy-7-desoxy-7-methoxy-daunomycinone (VII, configuration 9S; $R_1=R_2=R_3=H$) prepared as in Example 4 were dissolved in 60 ml. of trifluoroacetic acid and left overnight at room temperature. The solution was evaporated in vacuo, the residue taken up in 150 ml. of acetone and 60 ml. of 5% NAHCO₃ were added. The solution was left at room temperature for 30 minutes., then diluted with water and extracted repeatedly with chloroform. Evaporation of the solvent left a residue that was chromatographed on silica gel. On elution with chloroform, 0.6 gm. of 4-demethoxy-daunomycinone (VIII', $R_1=R_2=R_3=H$; m.p. 185°–187°; $[\alpha]_D^{20} + 165°$, c = 0.1, dioxane) and 0.5 gm. of 4-demethoxy-7-epi-daunomycinone (VIII'''; $R_1=R_2=R_3=H$); $[\alpha]_D^{20} - 86°$; (c = 0.1, dioxane) were collected.

EXAMPLE 6

4-Demethoxy-daunomycinone (VIII'; $R_1=R_2=R_3=H$).

When 4-demethoxy-7-epi-daunomycinone (Example 5) was treated with trifluoroacetic acid in the manner reported in Example 5 for 4-demethoxy-7-desoxy-7-methoxy-daunomycinone, there was obtained 4-demethoxy-daunomycinone in 48% yield.

EXAMPLE 7

4-Demethoxy-7,9-bis-epi-daunomycinone (VIII''; $R_1=R_2=R_3=H$).

Operating as in Examples 4 and 5, but employing 4-demethoxy-7-desoxy-9-epi-daunomycinone dimethylether (Example 3), there was obtained 4-demethoxy-7,9-bis-epi-daunomycinone, m.p. 185°–187°; $[\alpha]_D^{20} - 167°$, c = 0.1, dioxane.

EXAMPLE 8

α(−)-Daunosaminyl-4-demethoxy-daunomycinone (4-demethoxydaunomycin) (X; $R_1=R_2=R_3=R_5=H$) and β(−)-daunosaminyl-4-demethoxy-daunomycinone (β-4-demethoxy-daunomycin) (X'; $R_1=R_2=R_3=R_5=H$).

To 1 gm. of 4-demethoxydaunomycinone (Example 5) in 200 ml. of benzene, 3 gm. of 1,2,3,6-tetradeoxy-4-O-trifluoroacetyl-3-trifluoroacetamido-L-lyxo-hex-1-enepyranose* and 30 mg. of p-toluenesulfonic acid were added. The solution was refluxed for 8 hrs. in the dark.

Pyridine (0.1 ml.) was added and the solution evaporated in vacuo. The residue was taken up in chloroform, washed with water and 5% NaHCO$_3$. The solvent was evaporated in vacuo, the residue dissolved in 350 ml. of methanol and left overnight at room temperature. After evaporation of the solvent the residue was chromatographed on 20 gm. of silica gel, eluting first with chloroform, then with chloroform:acetone - 19:1 to give 0.6 gm. of α(−)-daunosaminyl-4-demethoxy-daunomycinone N-trifluoroacetate (X; $R_1=R_2=R_3=H$; $R_5=COCF_3$; m.p. 155°-158°; $[\alpha]_D^{20} + 200°$, c = 0.1, dioxane) and 0.30 gm. of β(−)daunosaminyl-4-demethoxy-daunomycinone N-trifluoroacetate (X'; $R_1=R_2=R_3=H$; $R_5=COCF_3$; m.p. 148°-150° C; $[\alpha]_D^{20} + 100°$, c = 0.1 dioxane). Compound X ($R_1=R_2=R_3=H$; $R_5=COCF_3$) was dissolved in 40 ml. of 0.1 N NaOH and kept at room temperature for 30 minutes. The solution was brought to pH 8 with HCl and extracted with chloroform. Evaporation of the solvent left a residue that was taken up in a little chloroform-methanol. Methanolic 0.1N HCl was added to adjust the pH to 4.5, after which sufficient ethyl ether was added to precipitate 0.35 gm. of the hydrochloride of α-(−)-daunosaminyl-4-demethoxy-daunomycinone (4-demethoxy-daunomycin).

*Prepared in accordance with Example 2 of application, Ser. No. 568,437, filed Apr. 16, 1975, now abandoned.

(X; $R_1=R_2=R_3=R_5=H$; m.p. 183°-185°; $[\alpha]_D^{20} + 210°$, c = 0.1, CH$_3$OH). From Compound X' ($R_1=R_2=R_3=H$; $R_5=COCF_3$) and operating in an analogous manner, the hydrochloride of β(−)-daunosaminyl-4-demethoxy-daunomycinone (β-4-demethoxy-daunomycin) (XI'; $R_1=R_2=R_3=R_5=H$; $[\alpha]_D^{20} + 124°$, c = 0.1 C$_2$H$_5$OH) was obtained.

EXAMPLE 9

α-(−)-Daunosaminyl-4-demethoxy-daunomycinone (4-demethoxydaunomycin) (X; $R_1=R_2=R_3=R_5=H$).

To a solution of 1 gm. of 4-demethoxy-daunomycinone (Example 5) in 230 ml. of anhydrous chloroform, 2.2 gm. of 2,3,6-trideoxy-3-trifluoroacetamido-4-O-trifluoroacetyl-α-L-lyxopyranosyl-chloride*,2 gm. of HgO, 0.5 gm. of HgBr$_2$ and 15 gm. of 5A molecular sieve were added under stirring. The suspension was stirred in the dark for 24 hours, filtered, concentrated in vacuo and the residue dissolved in 350 ml. of methanol. The solution was left overnight at room temperature. After evaporation of the solvent the residue was chromatographed on 20 gm. of silica gel, eluting first with chloroform, then with chloroform:acetone 19:1 to give 0.55 gm. of a-(−)-daunosaminyl-4-demethoxy-daunomycinone N-trifluoroacetate (X; $R_1=R_2=R_3=H$; $R_5=COCF_3$), which is then worked up as in Example 8, to give α-(−)-daunosaminyl-4-demethoxy-daunomycinone hydrochloride. (X; $R_1=R_2=R_3=R_5=H$).

*Prepared in accordance with Example 2 of copending application, Ser. No. 560,105, filed Mar. 19, 1975, now U.S. Pat. No. 4,039,663.

EXAMPLE 10

α-(−)-Daunosaminyl-4-demethoxy-7,9-bis-epi-daunomycinone
(α-7,9-bis-epi-4-demethoxy-daunomycin) (XI; $R_1=R_2=R_3=R_5=H$) and
β-(−)-daunosaminyl-4-demethoxy-7,9-bis-epi-daunomycinone
(β-7,9-bis-epi-4-demethoxy-daunomycin) (XI'; $R_1=R_2=R_3=R_5=H$).

Condensation of 4-demethoxy-7,9-bis-epi-daunomycinone (Example 7) with 1,2,3,6-tetradeoxy-4-O-trifluoroacetyl-3-trifluoroacetamido-L-lyxo-hex-1-enepyranose as described in Example 8, produced α-7,9-bis-epi-4-demethoxy-daunomycin N-trifluoroacetate (XI; $R_1=R_2=R_3=H$; $R_5=COCF_3$; m.p. 210°-215°; $[\alpha]_D^{20} - 91°$, c = 0.1, dioxane) together with β-7,9-bis-epi-4-demethoxy-daunomycin N-trifluoroacetate (XI'; $R_1=R_2=R_3$50 H; $R_5=COCF_3$; m.p. 165°-167°; $[\alpha]_D^{20} - 270°$, c = 0.1, dioxane). These compounds were separated by chromatography on silica gel column using chloroform: acetone (80:20 by volume) as the eluent. The subsequent hydrolysis of said compounds with 0.1 N NaOH as reported in Example 8, produced respectively α-7,9-bis-epi-4-demethoxy-daunomycin hydrochloride (XI; $R_1=R_2=R_3=R_5=H$; m.p. 205°-207°; $[\alpha]_D^{20} - 80°$, c = 0.1, CH$_3$OH) and β-7,9-bis-epi-4-demethoxy-daunomycin hydrochloride (XI'; $R_1=R_2=R_3=R_5=H$; m.p. 185°-187°; $[\alpha]_D^{20} - 250°$, c = 0.1, CH$_3$OH).

EXAMPLE 11

Daunomycinone (VIII'; $R_1=R_3=H$; $R_2=OCH_3$).

Condensation of 3-methoxyphthalic acid monomethyl ester monochloride with (−)-1,4-dimethoxy-6-hydroxy-6-acetyl-tetralin as described in Example 2 produced 7-desoxy-daunomycinone dimethyl ether (IV, configuration 9S; $R_1=R_3=H$; $R_2=OCH_3$; $[\alpha]_D^{20} - 37°$, c = 1, CHCl$_3$) which was treated as described in Example 4 to give 7-(S)-methoxy-7-desoxy-daunomycinone dimethyl ether, which by treatment with AlCl$_3$, as described above, and in applicants' U.S. Pat. No. 3,963,760 which corresponds to British Pat. No. 1461190, yielded 7-(S)-methoxy-7-desoxy-daunomycinone. Treatment of this compound with trifluoroacetic acid as described in Example 5 produced daunomycinone (VIII'; $R_1=R_3=H$; $R_2=OCH_3$; m.p. 210°-213°, $[\alpha]_D^{20} + 175°$, c = 0.1, dioxane).

EXAMPLE 12

7,9-bis-epi-Daunomycinone (VIII''; $R_1=R_3=H$; $R_2=OCH_3$).

Operating as described in Example 11, but employing (+)-1,4-dimethoxy-6-hydroxy-6-acetyl-tetralin, there was obtained 7,9-bis-epi-daunomycinone (VIII''; $R_1=R_3=H$; $R_2=OCH_3$; m.p. 210°-213°; $[\alpha]_D^{20}$ 31 176°; c = 0.1 dioxane).

EXAMPLE 13

7,9-bis-epi-Daunomycin (XI; $R_1=R_3=H$; $R_2=OCH_3$; $R_5=H$).

Operating as described in Example 8, but employing 7,9-bis-epi-daunomycinone (Example 12), there was obtained 7,9-bis-epi-daunomycin (XI; $R_1=R_3=H$; $R_2=OCH_3$; $R_5=H$).

EXAMPLE 14

1-Methoxydaunomycinone (VIII'; $R_1$=H; $R_2$=$R_3$=$OCH_3$).

Condensation of 3,6-dimethoxyphthalic acid monomethyl ester monochloride with (−)-1,4-dimethoxy-6-hydroxy-6-acetyl-tetralin as described in Example 11, gave 1-methoxydaunomycinone (VIII', $R_1$=H; $R_2$=$R_3$=$OCH_3$).

EXAMPLE 15

1-Methoxydaunomycin (X; $R_1$=$R_5$=H; $R_2$=$R_3$=$OCH_3$).

Operating as described in Example 8, but employing 1-methoxy-daunomycinone (Example 14), there was obtained 1-methoxy-daunomycin (X; $R_1$=$R_5$=H; $R_2$=$R_3$=$OCH_3$).

EXAMPLE 16

1-Methoxy-7,9-bis-epi-daunomycinone (VIII"; $R_1$=H; $R_2$=$R_3$=$OCH_3$).

Operating as described in Example 14, but employing (+)-1,4-dimethoxy-6-hydroxy-6-acetyl-tetralin, there was obtained 1-methoxy-7,9-bis-epi-daunomycinone (VIII"; $R_1$=H; $R_2$=$R_3$=$OCH_3$).

EXAMPLE 17

1-Methoxy-7,9-bis-epi-daunomycin (XI; $R_1$=$R_5$=H; $R_2$=$R_3$=$OCH_3$).

Operating as described in Example 8, but employing 1-methoxy-7,9-bis-epi-daunomycinone (Example 16), there was obtained 1-methoxy-7,9-epi-daunomycin (XI; $R_1$=$R_5$=H; $R_2$=$R_3$=$OCH_3$).

EXAMPLE 18

4-Demethoxy-1,4-dimethyl-daunomycinone (VIII'; $R_1$=H; $R_2$=$R_3$=$CH_3$).

Condensation of 3,6-dimethylphthalic acid monomethyl ester monochloride with (−)-1,4-dimethoxy-6-hydroxy-6-acetyl-tetralin as described in Examples 2, 4 and 5, yielded 4-demethoxy-1,4-dimethyl-daunomycinone (VIII', $R_1$=H; $R_2$=$R_3$=$CH_3$).

EXAMPLE 19

4-Demethoxy-1,4-dimethyl-7,9-bis-epi-daunomycinone (VIII"; $R_1$=H; $R_2$=$R_3$=$CH_3$).

Operating as described in Example 18, but employing (+)-1,4-dimethoxy-6-hydroxy-6-acetyl-tetralin, there was obtained 4-demethoxy-1,4-dimethyl-7,9-bis-epi-daunomycinone (VIII"; $R_1$=H; $R_2$=$R_3$=$CH_3$).

EXAMPLE 20

4-Demethoxy-1,4-dimethyl-daunomycin (X; $R_1$=$R_5$=H; $R_2$=$R_3$=$CH_3$).

Operating as described in Example 8, but employing 4-demethoxy-1,4-dimethyl-daunomycinone (Example 18), there was obtained 4-demethoxy-1,4-dimethyl-daunomycin (X; $R_1$=$R_5$=H; $R_2$=$R_3$=$CH_3$).

EXAMPLE 21

4-Demethoxy-1,4-dimethyl-7,9-bis-epi-daunomycin (XI; $R_1$=$R_5$=H; $R_2$=$R_3$=$CH_3$).

Operating as described in Example 20, but employing 4-demethoxy-1,4-dimethyl-7,9-bis-epi-daunomycinone (Example 19), there was obtained 4-demethoxy-1,4-dimethyl-7,9-bis-epi-daunomycin (XI; $R_1$=$R_5$=H; $R_2$=$R_3$=$CH_3$).

EXAMPLE 22

4-Demethoxy-1,4-dichloro-daunomycinone (VIII'; $R_1$=H; $R_2$=$R_3$=Cl).

Condensation of 3,6-dichlorophthalic acid monomethyl ester monochloride with (−)-1,4-dimethoxy-6-hydroxy-6-acetyl-tetralin as described in Examples 2, 4 and 5, yielded 4-demethoxy-1,4-dichloro-daunomycinone (VIII'; $R_1$H; $R_2$=$R_3$=Cl).

EXAMPLE 23

4-Demethoxy-1,4-dichloro-7,9-bis-epi-daunomycinone (VIII"; $R_1$=H; $R_2$=$R_3$=Cl).

Operating as described in Example 22 but employing (+)-1,4-dimethoxy-6-hydroxy-6-acetyl-tetralin, there was obtained 4-demethoxy-1,4-dichloro-7,9-bis-epi-daunomycinone (VIII"; $R_1$=H; $R_2$=$R_3$=Cl).

EXAMPLE 24

4-Demethoxy-1,4-dichloro-daunomycin (X; $R_1$=$R_5$=H; $R_2$=$R_3$=Cl).

Operating as in Example 8, but employing 4-demethoxy-1,4-dichloro-daunomycinone (Example 22), there was obtained 4-demethoxy-1,4-dichloro-daunomycin (X; $R_1$=$R_5$=H; $R_2$=$R_3$=Cl).

EXAMPLE 25

4-Demethoxy-1,4-dichloro-7,9-bis-epi-daunomycin (XI; $R_1$=$R_5$=H; $R_2$=$R_3$=Cl).

Operating as in Example 8, but employing 4-demethoxy-1,4-dichloro-7,9-bis-epi-daunomycinone (Example 23), there was obtained 4-demethoxy-1,4-dichloro-7,9-bis-epi-daunomycin (XI: $R_1$=$R_5$=H; $R_2$=$R_3$=Cl).

EXAMPLE 26

4-Demethoxy-1,4-dibromo-daunomycinone (VIII'; $R_1$=H, $R_2$=$R_3$=Br).

Condensation of 3,6-dibromophthalic acid monoethyl ester monochloride with (−)-1,4-dimethoxy-6-hydroxy-6-acetyl-tetralin as described in Examples 2, 4 and 5, yielded 4-demethoxy-1,4-dichloro-daunomycinone (VIII'; $R_1$=H; $R_2$=$R_3$=Br).

EXAMPLE 27

4-Demethoxy-1,4-dibromo-7,9-bis-epi-daunomycinone (VIII"; $R_1$=H; $R_2$=$R_3$=Br).

Operating as described in Example 26, but employing (+)-1,4-dimethoxy-6-hydroxy-6-acetyl-tetralin, there was obtained 4-demethoxy-1,4-dibromo-7,9-bis-epi-daunomycinone (VIII"; $R_1$=H; $R_2$=$R_3$=Br).

EXAMPLE 28

4-Demethoxy-1,4-dibromo-daunomycin (X; $R_1$=$R_5$=H; $R_2$=$R_3$=Br).

Operating as in Example 8, but employing 4-demethoxy-1,4-dibromo-daunomycinone (Example 26), there was obtained 4-demethoxy-1,4-dibromo-daunomycin (X; $R_1$=$R_5$=H; $R_2$=$R_3$=Br).

EXAMPLE 29

4-Demethoxy-1,4-dibromo-7,9-bis-epi-daunomycin (XI; $R_1=R_5=H$; $R_2=R_3=Br$).

Operating as in Example 8, but employing 4-demethoxy-1,4-dibromo-7,9-bis-epi-daunomycinone (Example 27), there was obtained 4-demethoxy-1,4-dibromo-7,9-bis-epi-daunomycin (XI; $R_1=R_5=H$; $R_2=R_3=Br$).

EXAMPLE 30

4-Demethoxy-2,3-dimethyl-daunomycinone (VIII'; $R_1=CH_3$; $R_2=R_3=H$).

Condensation of 4,5-dimethylphthalic acid monomethyl ester monochloride with (−)-1,4-dimethoxy-6-hydroxy-6-acetyl-tetralin as described in Example 2, yielded 4-demethoxy-2,3-dimethyl-daunomycinone dimethyl ether; m.p. 158°–160°, $[\alpha]_D^{20} - 40°$ (c = 0.1, $CHCl_3$). By bromination and trifluoroacetic acid treatment as described in Examples 4 and 5, there were obtained, after chromatographic separation on silica gel, 4-demethoxy-2,3-dimethyl-daunomycinone, (VIII'; $R_1=CH_3$; $R_2=R_3+H$); m.p. 208°–210°, $[\alpha]_D^{20} + 160°$, c = 0.1, $CHCl_3$; and 4-demethoxy-7-epi-2,3-dimethyl-daunomycinone (VIII'''; $R_1=CH_3$; $R_2=R_3=H$); $[\alpha]_D^{20} - 80°$; c = 0.1, $CHCl_3$.

EXAMPLE 31

4-Demethoxy-2,3-dimethyl-7,9-bis-epi-daunomycinone (VIII''; $R_1=CH_3$; $R_2=R_3=H$).

Operating as described in Example 30, but employing (+)-1,4-dimethoxy-6-hydroxy-6-acetyl-tetralin, there was obtained 4-demethoxy-2,3-dimethyl-7,9-bis-epi-daunomycinone (VIII''; $R_1=CH_3$; $R_2=R_3=H$; m.p. 209°–210°; $[\alpha]_D^{20} - 162°$, c = 0.1, $CHCl_3$).

EXAMPLE 32

4-Demethoxy-2,3-dimethyl-daunomycin (X; $R_1=CH_3$; $R_2=R_3=H$).

Operating as described in Example 8, but employing 4-demethoxy-2,3-dimethyl-daunomycinone (Example 30), α-4-demethoxy-2,3-dimethyl-daunomycin N-trifluoroacetate was isolated (X; $R_1=CH_3$; $R_2=R_3=H$; $R_5=COCF_3$; m.p. 233°–235°; $[\alpha]_D^{20} + 181°$, c = 0.1, dioxane) from which, by subsequent hydrolysis with 0.1 N NaOH, there was obtained α-4-demethoxy-2,3-dimethyl-daunomycin hydrochloride (X; $R_1=CH_3$; $R_2=R_3=R_5=H$; m.p. 190°–192°; $[\alpha]_D + 180°$, c = 0.1 $CH_3OH$).

EXAMPLE 33

4-Demethoxy-2,3-dimethyl-7,9-bis-epi-daunomycin (XI; $R_1=CH_3$; $R_2=R_3=R_5=H$).

Operating as in Example 8, but employing 4-demethoxy-2,3-dimethyl-7,9-bis-epi-daunomycinone (Example 31), there was obtained 4-demethoxy-2,3-dimethyl-7,9-bis-epi-daunomycin hydrochloride (XI; $R_1=CH_3$; $R_2=R_3=R_5=H$).

EXAMPLE 34

4-Demethoxy-2,3-dimethoxy-daunomycinone (VIII'; $R_1=OCH_3$; $R_2=R_3=H$).

Condensation of 4,5-dimethyoxyphthalic acid monomethyl ester monochloride with (−)-1,4-dimethoxy-6-hydroxy-6-acetyl-tetralin as described in Example 11, gave 4-demethoxy-2,3-dimethoxy-daunomycinone (VIII'; $R_1=OCH_3$, $R_2R_3=H$).

EXAMPLE 35

4-Demethoxy-2,3-dimethoxy-7,9-bis-epi-daunomycinone (VIII''; $R_1=OCH_3$; $R_2=R_3=H$).

Operating as in Example 34, but employing (+)-1,4-dimethoxy-6-hydroxy-6-acetyl-tetralin, there was obtained 4-demethoxy-2,3-dimethoxy-7,9-bis-epi-daunomycinone (VIII''; $R_1=OCH_3$; $R_2=R_3=H$).

EXAMPLE 36

4Demethoxy-2,3-dimethoxy-daunomycin (X; $R_1=OCH_3$ $R_2=R_3=R_5=H$).

Operating as in Example 8, but employing 4-demethoxy-2,3-dimethoxydaunomycinone (Example 34), there was obtained 4-demethoxy-2,3-dimethoxy-daunomycin hydrochloride (X; $R_1=OCH_3$; $R_2=R_3=R_5=H$).

EXAMPLE 37

4-Demethoxy-2,3-dimethoxy-7,9-bis-epi-daunomycin (XI; $R_1=OCH_3$; $R_2=R_3=R_5=H$).

Operating as in Example 8, but employing 4-demethoxy-2,3-dimethoxy-7,9-bis-epi-daunomycinone (Example 35), there was obtained 4-demethoxy-2,3-dimethoxy-7,9-bis-epi-daunomycin hydrochloride (XI; $R_1=OCH_3$; $R_2=R_3=R_5=H$).

EXAMPLE 38

4-Demethoxy-2,3-dichloro-daunomycinone (VIII'; $R_1=Cl$; $R_2=R_3=H$).

Condensation of 4,5-dichlorophthalic acid monomethyl ester monochloride with (−)-1,4-dimethoxy-6-hydroxy-6-acetyl-tetralin as described in Example 2, gave 4-demethoxy-2,3-dichloro-daunomycinone dimethyl ether; m.p. 168°–170°, $[\alpha]_D^{20} - 28°$ (c = 1, dioxane), which, by bromination and trifluoroacetic acid treatment as described in Examples 4 and 5, produced 4-demethoxy-2,3-dichlorodaunomycinone. (VIII'; $R_1=Cl$; $R_2=R_3=H$; m.p. 138°–140°).

EXAMPLE 39

4-Demethoxy-2,3-dichloro-7,9-bis-epi-daunomycinone (VIII''; $R_1=Cl$; $R_2=R_3=H$).

Operating as in Example 38, but employing (+)-1,4-dimethoxy-6-hydroxy-6-acetyl-tetralin, there was obtained 4-demethoxy-2,3-dichloro-7,9-bis-epi-daunomycinone (VIII''; $R_1=Cl$; $R_2=R_3=H$; m.p. 137°–139°).

EXAMPLE 40

4-Demethoxy-2,3-dichloro-daunomycin (X; $R_1=Cl$; $R_2=R_3=R_5=H$).

Operating as in Example 8, but employing 4-demethoxy-2,3-dichloro-daunomycinone (Example 38) α-4-demethoxy-2,3-dichloro-daunomycin N-trifluoroacetate (X; $R_1=Cl$; $R_2=R_3=H$; $R_5=COCF_3$; m.p. 238°–240°; $[\alpha]_D^{20} + 170°$, c = 0.1, dioxane) was isolated and from which by subsequent hydrolysis with 0.1 N NaOH, there was obtained α-4-demethoxy-2,3-dichloro-daunomycin hydrochloride (X; $R_1=Cl$; $R_2=R_3=R_5=H$; $[\alpha]_D^{20} + 180°$, c = 0.1, $CH_3OH$).

EXAMPLE 41

4-Demethoxy-2,3-dichloro-7,9-bis-epi-daunomycin (XI; $R_1$=Cl; $R_2$=$R_3$=$R_5$=H).

Operating as in Example 8, but employing 4-demethoxy-2,3dichloro-7,9-bis-epi-daunomycinone (Example 39), there was obtained 4-demethoxy-2,3-dichloro-7,9-bis-epi-daunomycin hydrochloride (XI; $R_1$=Cl; $R_2$=$R_3$=$R_5$=H).

EXAMPLE 42

4-Demethoxy-2,3-dibromo-daunomycinone (VIII'; $R_1$=Br; $R_2$=$R_3$=H).

Condensation of 4,5-dibromophthalic acid monomethyl ester monochloride with (−)-1,4-dimethoxy-6-hydroxy-6-acetyl-tetralin as described in Examples 2, 4 and 5, gave 4-demethoxy-2,3-dibromo-daunomycinone (VIII'; $R_1$=Br; $R_2$=$R_3$50 H).

EXAMPLE 43

4-Demethoxy-2,3dibromo-7,9-bis-epi-daunomycinone (VIII'; $R_1$=Br; $R_2$=$R_3$=H).

Operating as in Example 42, but employing (+)-1,4-dimethoxy-6-hydroxy-6-acetyl-tetralin, there was obtained 4-demethoxy-2,3-dibromo-7,9-bis-epi-daunomycinone (VIII''; $R_1$=Br; $R_2$=$R_3$=H).

EXAMPLE 44

4-Demethoxy-2,3-dibromo-daunomycin (X; $R_1$=Br; $R_2$=$R_3$=$R_5$=H).

Operating as in Example 8, but employing 4-demethoxy-2,3-dibromo-daunomycinone (Example 42), there was obtained 4-demethoxy-2,3-dibromo-daunomycin hydrochloride (X; $R_1$=Br; $R_2$=$R_3$=$R_5$=H).

EXAMPLE 45

4-Demethoxy-2,3-dibromo-7,9-bis-epi-daunomycin (XI; $R_1$=Br; $R_2$=$R_3$=$R_5$=H).

Operating as in Example 8, but employing 4-demethoxy-2,3-dibromo-7,9-bis-epi-daunomycinone (Example 43), there was obtained 4-demethoxy-2,3-dibromo-7,9-bis-epi-daunomycin hydrochloride (XI; $R_1$=Br; $R_2$=$R_3$=$R_5$=H).

EXAMPLE 46

(+)-4-Demethoxy-7-desoxy-daunomycinone dimethyl ether (IV; $R_1$=$R_2$=$R_3$=H).

To 5 gm. of (+)-1,4-dimethoxy-6-hydroxy-6-acetyl-tetralin in 30 ml. of trifluoroacetic anhydride, 10 gm. of phthalic acid monomethyl ester were added and the solution refluxed for 18 hrs. The solution was evaporated in vacuo and the residue taken up in 100 ml. of 60% ethanol containing 8 gm. of NaOH. The solution was kept at 60° for 1 hr., diluted with water and extracted with chloroform which was then discarded. The aqueous solution was acidified with 2 N HCl and extracted with chloroform. Evaporation of the solvent left a residue that was dissolved in 20 ml. of liquid HF. After 3 hrs., the HF was evaporated and the residue taken up in chloroform. The chloroform extracts were washed with water and dilute NaOH and evaporated in vacuo. The residue was crystallized from ether to give 1.5 gm. of racemic 4-demethoxy-7-desoxy-daunomycinone dimethyl ether (IV; $R_1$=$R_2$=$R_3$=H; m.p. 184°–185°).

Variations and modifications can, of course, be made without departing from the spirit and scope of the invention.

Having thus described our invention what we desire to secure by Letters Patent and hereby claim is:

1. Optically active anthracyclinones of the formulae IV' and IV'''

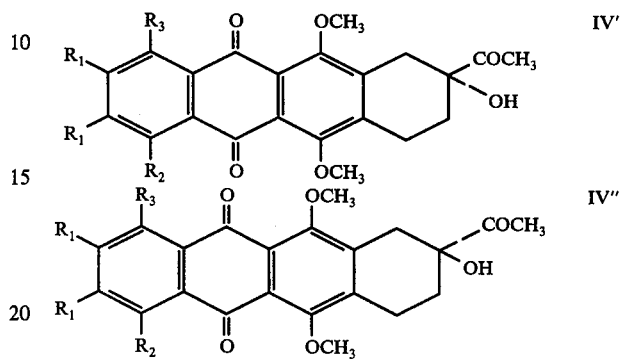

wherein $R_1$ is hydrogen and $R_2$ and $R_3$ are the same and are hydrogen, methyl, methoxy, chlorine or bromine; or $R_2$ and $R_3$ are both hydrogen and $R_1$ is methyl, methoxy, chlorine or bromine; or $R_1$ and $R_3$ are both hydrogen and $R_2$ is methoxy with the proviso that $R_1$, $R_2$ and $R_3$ are not all simultaneously hydrogen in the case of formula IV'.

2. An optically active anthracyclinone of the general formula VIII', VIII'', VIII''' or VIII'''':

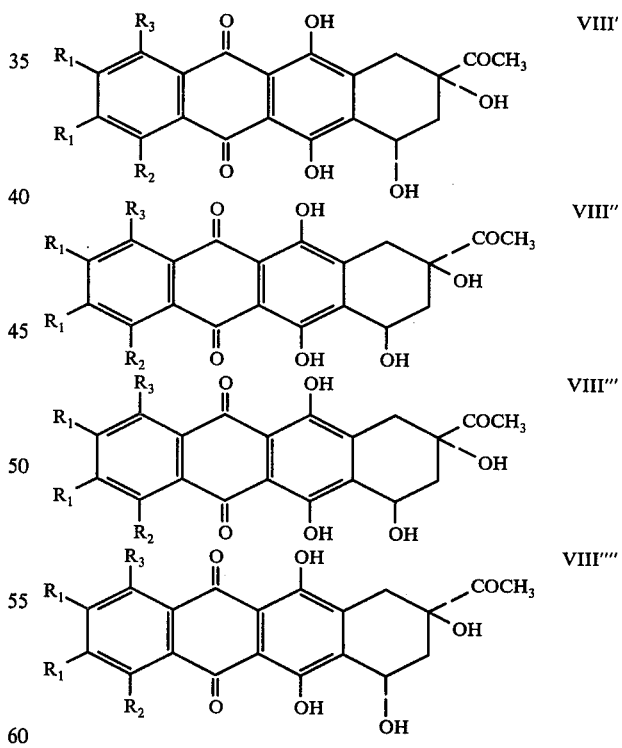

wherein $R_1$ is hydrogen and $R_2$ and $R_3$ are the same and are hydrogen, methyl, methoxy, chlorine or bromine; or $R_2$ and $R_3$ are both hydrogen and $R_1$ is methyl, methoxy, chlorine or bromine; or, in the case of formulae VIII'', VIII''' and VIII'''', $R_1$ and $R_3$ are both hydrogen and $R_2$ is methoxy.

* * * * *

UNITED STATES PATENT OFFICE
CERTIFICATE OF CORRECTION

Patent No. 4,077,988  Dated March 7, 1978

Inventor(s) Federico Arcamone et al

It is certified that error appears in the above-identified patent and that said Letters Patent are hereby corrected as shown below:

Column 3, line 55: "diasteroisomeric" should read -- diastereoisomeric --; line 67: "keton" should read -- ketol --.

Column 4, line 29: "appropriatee" should read -- appropriate --.

Column 6, line 13: "ketoln" should read -- ketol --.

Column 12, line 20: "$R_1=R_2=R_3 50$" should read -- $R_1=R_2=R_3=H$ --; line 58: "$[\alpha]_D^{20} 31\ 176°;$" should read -- $[\alpha]_D^{20} -176°;$ --.

Column 14, line 12: "$R_1H;$" should read -- $R_1=H;$ --.

Column 15, line 23: "$R_2=R_3+H);$" should read -- $R_2=R_3=H);$ --; line 40: "$R_2=R_3=H).$" should read -- $R_2=R_3=R_5=H).$ --; line 50: "$[\alpha]_D^{\circ}$" should read -- $[\alpha]_D^{20}$ --.

Column 16, lines 14-15: "4Demethoxy-2,3-dimethoxy-daunomycin (X; $R_1=OCH_3 R_2=R_3=R_5=H).$" should read -- 4-Demethoxy-2,3-dimethoxy-daunomycin (X; $R_1=OCH_3; R_2=R_3=R_5=H).$ --.

Column 17, line 19: "$R_2=R_3 50\ H).$" should read -- $R_2=R_3=H).$ --.

UNITED STATES PATENT OFFICE
CERTIFICATE OF CORRECTION

Patent No. 4,077,988  Dated March 7, 1978

Inventor(s) Federico Arcamone et al

It is certified that error appears in the above-identified patent and that said Letters Patent are hereby corrected as shown below:

Column 17, lines 48-49: "(+)-4-Demethoxy-7-desoxy-daunomycinone dimethyl ether (IV; $R_1=R_2=R_3=H$)." should read -- ($\pm$)-4-Demethoxy-7-desoxy-daunomycinone dimethyl ether (IV; $R_1=R_2=R_3=H$). --.

Signed and Sealed this

Twenty-seventh Day of February 1979

[SEAL]

Attest:

RUTH C. MASON
Attesting Officer

DONALD W. BANNER
Commissioner of Patents and Trademarks